US005690678A

United States Patent [19]
Johnson

[11] Patent Number: 5,690,678
[45] Date of Patent: Nov. 25, 1997

[54] ARRANGEMENT FOR ANCHORING SUTURE TO BONE

[76] Inventor: Lanny L. Johnson, 2950 E. Mount Hope Rd., Okemos, Mich. 48864

[21] Appl. No.: 640,232

[22] Filed: Apr. 30, 1996

[51] Int. Cl.⁶ .................................................. A61B 17/04
[52] U.S. Cl. .......................... 606/232; 606/233; 606/72; 606/187; 128/898
[58] Field of Search ........................... 606/232-3, 228, 606/139, 144, 145, 148, 142, 151, 72, 75, 187; 623/13; 128/898

[56] References Cited

U.S. PATENT DOCUMENTS

| | | |
|---|---|---|
| 477,225 | 6/1892 | Rauhe . |
| 2,354,639 | 7/1944 | Seymour . |
| 3,112,563 | 12/1963 | Kamborian et al. . |
| 3,123,881 | 3/1964 | Westman . |
| 3,427,772 | 2/1969 | Williams . |
| 3,976,079 | 8/1976 | Samuels et al. ............... 606/232 |
| 4,258,464 | 3/1981 | Ullman, Jr. . |
| 4,593,734 | 6/1986 | Wallace . |
| 4,850,084 | 7/1989 | Iwasaki . |
| 5,041,129 | 8/1991 | Hayhurst et al. . |
| 5,046,513 | 9/1991 | Gattuma et al. . |
| 5,203,787 | 4/1993 | Noblitt et al. . |
| 5,269,809 | 12/1993 | Hayhurst et al. . |
| 5,403,348 | 4/1995 | Bonutti . |
| 5,405,359 | 4/1995 | Pierce . |
| 5,417,691 | 5/1995 | Hayhurst . |
| 5,499,667 | 3/1996 | Nakanishi . |
| 5,507,331 | 4/1996 | Nakanishi . |

Primary Examiner—Michael Buiz
Assistant Examiner—Daphna Shai
Attorney, Agent, or Firm—Cushman Darby & Cushman, IP Group of Pillsbury Madison & Sutro LLP

[57] ABSTRACT

A bore is provided in bone, the bore communicating with a slot provided in the bone's cortical layer and with a channel of larger size than the slot located in cancellous bone below the slot. The slot overlays the channel and is in communication therewith. A length of suture is knotted to a size greater than the width of the slot, and the knot is introduced to the channel via the bore. The remainder of the suture is passed through the slot whereby the length of suture is anchored in the bone. Instead of knotting the suture, it can be attached to a bead having a diameter greater than the width of the slot, the bead being received within the channel to again anchor the suture.

13 Claims, 2 Drawing Sheets

ARRANGEMENT FOR ANCHORING SUTURE TO BONE

BACKGROUND OF THE INVENTION

1. Field of the Invention

The present invention relates to an arrangement for anchoring surgical suture to bone.

2. Description of the Prior Art

Various surgical procedures require soft tissue, such as ligaments, tendons, muscles and the like to be attached to bone. This typically is accomplished by securing a suture anchor to the bone and then using suture which is joined to the anchor to attach the tissue to the bone.

A number of different devices for anchoring suture to bone are known. One such device consists of a staple-like component having at least two leg portions and a body disposed between the legs. The legs are driven into the bone and the suture is anchored between the bone and the body of the staple.

Another type of suture is disclosed in U.S. Pat. No. 5,141,520. This anchor consists of a cylindrical body and a solid conical-shaped harpoon-type head attached to the body. A suture end is secured within the body, and the head is driven into the bone.

In other types of suture anchor devices the anchor is not driven directly into the bone but instead is placed within a bore formed in the bone. An example, disclosed in U.S. Pat. Nos. 4,898,156 and 5,046,513, consists of a metal cylindrical body having at least one flexible tail or barb extending from a free end thereof. As the body and barb are inserted into a bore formed in the bone, the barb flexes in such a way as to engage the side wall of the bore thereby securing the anchor within the bore.

All of the devices just described are of the type wherein an anchoring component includes elements which grip the bone in order to secure the anchor in place. Consequently, such known devices are dependent on the degree of fastening achieved between the bone and the gripping elements. This capability is subject to the skill of the surgeon utilizing such devices and the locations where the devices are developed. Moreover, the number and configuration of suture ends which can be accommodated by such known suture anchors are dependent on the design of each anchor, and this can limit the suitability of a given anchor to specific applications.

It has been proposed to reduce dependence on gripping elements which dig into bone so as to secure the anchor by employing a different technique wherein an anchor is passed through cortical bone and is manipulated in such a manner that a portion of the anchor underlies the cortical bone thereby preventing the anchor from being separated from the bone. Such arrangements are disclosed, for example, in U.S. Pat. Nos. 5,041,129, 5,269,809 and 5,403,348.

The present invention generally is of the type wherein anchoring is achieved through the utilization of the underside of cortical bone to retain the suture.

SUMMARY OF THE INVENTION

According to the present invention, bone is bored to a depth below the cortical layer of the bone. An elongated slot is formed in the cortical layer so as to overlay a channel of larger diameter simultaneously formed beneath the cortical layer. Suture material is knotted to a size greater than the width of the slot, and the knot is passed through the bore and along the channel to underlay the slot. With the suture end(s) passing through the slot and tension applied thereto, the knot anchors the suture to the bone. Alternatively, instead of knotting the suture, the suture extends through a passage in a bead, or into an external slot in such bead. The bead is sized so as to be received within the channel without being able to be pulled through the slot in the cortical bone. The suture end(s) extend through the slot whereby on application of tension, the bead is drawn up against the underside of the slot to anchor the suture.

The invention now will be described in greater detail with respect to the accompanying drawings illustrating preferred embodiments of the invention.

DETAILED DESCRIPTION OF THE INVENTION

Figure 1A:
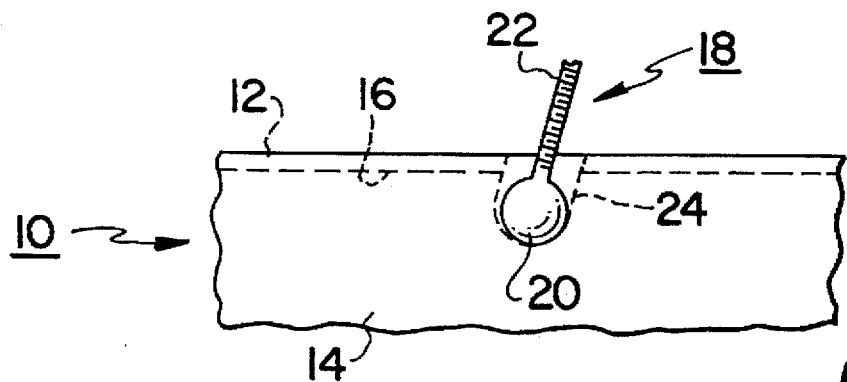
FIGS. 1A–1C schematically illustrate the forming of a bore, a channel and a slot in a segment of bone.
Figure 1B:
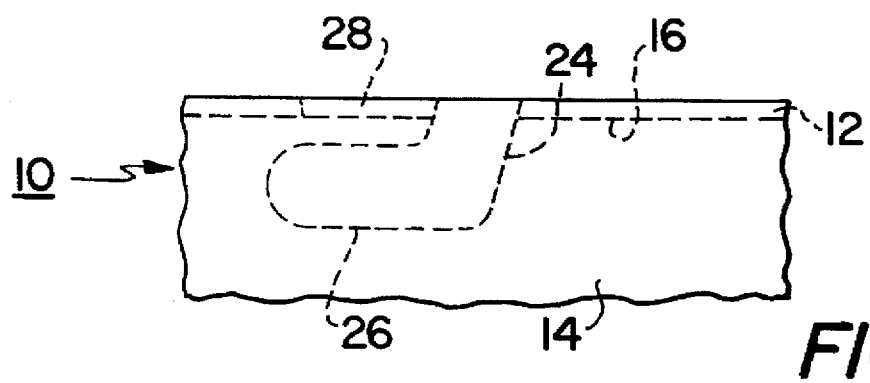
Figure 1C:
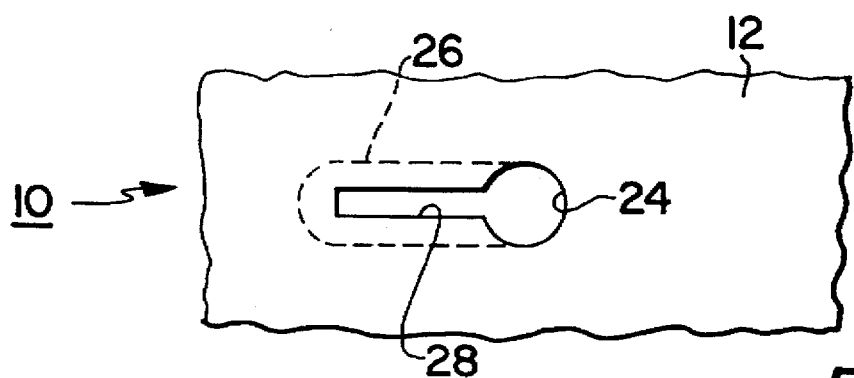

Referring to FIGS. 1A–1C, a piece of bone is schematically illustrated as 10. The bone includes an upper cortical layer, generally indicated as 12, overlaying cancellous bone identified as 14. For convenience of illustration, the interface between layers 12 and 14 is shown as a broken line 16.

In FIG. 1A, a cutting tool 18 is illustrated. The tool includes a spherical end portion 20 and a cylindrical shaft portion 22. Such a tool performs functions analogous to those performed by separate tools in woodworking applications. Of course, the cutting surfaces formed on portions 20 and 22 are specifically designed so as to efficiently cut bone. To facilitate positioning of the tool 18 relative to the cortical layer 12 for achieving proper location of a bore formed in the bone, the spherical portion 20 is provided with a conical projection (not shown) at the distal end of the tool.

The tool 18 is joined to a drill (not shown) which rotates the tool about the longitudinal axis of portion 22. When force is applied in a downwardly direction, as shown in FIG. 1A, a bore 24 is formed in the bone. The bore extends from the surface of bone 10 to a depth at which the spherical portion 20 of the drill is fully within the cancellous bone 14 slightly below the cortical layer 12. As shown in FIG. 1B, when the tool is then moved in a direction parallel to interface 16, portion 20 cuts a channel 26 of circular cross-section in the cancellous bone. Simultaneously, portion 22 cuts a slot 28 in the cortical bone which communicates with channel 26. As shown in FIG. 1C, slot 28 overlays channel 26 and has a narrower width than the channel.

Figure 2:
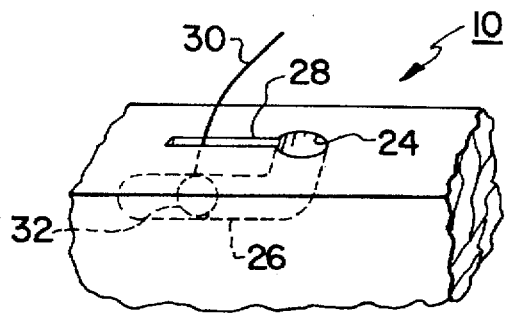
FIG. 2 schematically illustrates the anchoring of a single suture end in the bone.
Figure 3:
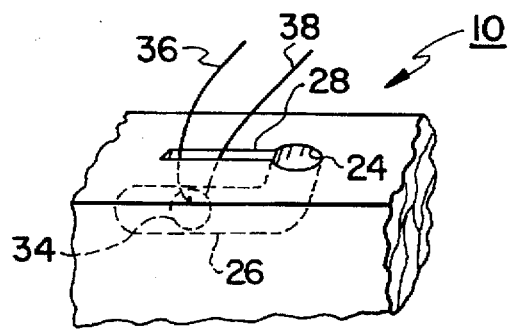
FIG. 3 schematically illustrates the anchoring of a pair of suture ends in the bone.
Figure 4:
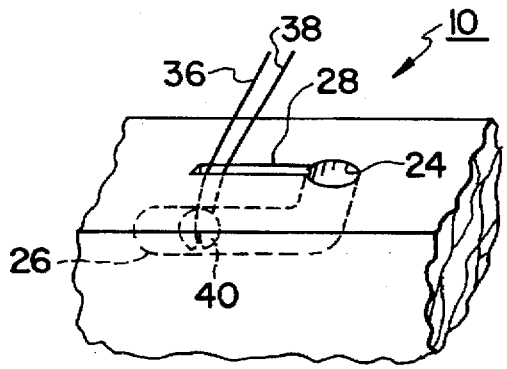
FIG. 4 schematically illustrates an alternative for anchoring a pair of suture ends in the bone.

With the bore, channel and slot having been so formed, the bone is prepared for the anchoring of suture in ways to be described with respect to FIGS. 2–4.

In FIG. 2, a single length of suture 30 is shown. The suture is provided with a knot 32 at its end, the knot being narrower than the bore 24 and channel 26 but wider than slot 28. Consequently, when the knot is introduced to channel 26 through bore 24, and with the free end of the suture placed under tension, the knot 32 is elevated to the top of channel 26 but proceeds no farther because of the narrower slot 28. The suture thus is anchored, and its free end can be used by the surgeon to secure tissue to the bone 10.

The embodiment shown in FIG. 3 differs from that of FIG. 2 only in that a length of suture is knotted intermediate its ends at 34 whereby two anchored ends 36 and 38 pass through slot 28 so as to be available to the surgeon.

In the embodiment of FIG. 4, the suture is not knotted. Instead, it is secured to a bead 40 which is introduced to channel 26 via bore 24 after a length of suture has been joined to the bead. Otherwise, the suture is anchored within the bone 10 in the same manner as described with respect to FIG. 3.

Figure 5:
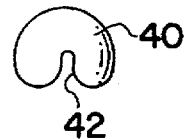
FIG. 5 illustrates a first embodiment of a bead suitable for use in the alternative anchoring arrangement shown in FIG. 4.
Figure 6:
FIG. 6 illustrates a second embodiment of a bead suitable for use in the alternative anchoring arrangement shown in FIG. 4.

Beads of spherical or non-spherical configuration may be used in practicing the present invention. Two types of bead 40 are shown in FIGS. 5 and 6. In FIG. 5, the exterior of the bead is slotted at 42 to accept and retain a length of suture intermediate its ends. Alternatively, FIG. 6 is provided with an internal passage 44 through which the suture is threaded.

Figure 7:
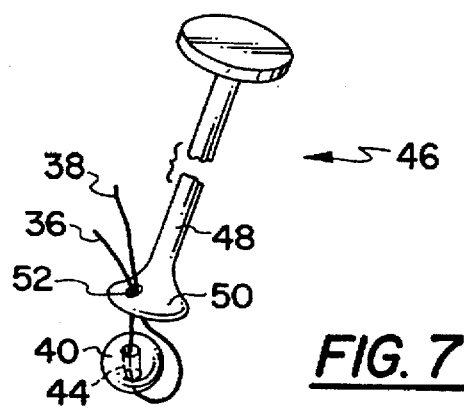
FIG. 7 illustrates a tool suitable for inserting the bead which is shown in FIGS. 5 and 6 into a channel formed in the bone.

To facilitate the introduction of bead 40 into channel 26, an insertion tool 46 is provided. The tool, shown in FIG. 7, includes a bottom portion 48 having a concave cup segment 50 at its end. Segment 50 is provided with a passage 52. In operation, one of the ends 36 and 38 of a length of suture is threaded through passage 44 in bead 40, and the two ends 36 and 38 are threaded through passage 52. The surgeon applies tension to ends 36 and 38 to draw the bead 40 within cup 50. The tool then is moved to the bore 24, and the bead is inserted first into the bore and then into channel 26. As this occurs, the surgeon threads the suture ends 36 and 38 along slot 28. With the bead substantially in place, tool 46 is withdrawn. The surgeon relaxes the tension on ends 36 and 38 so that the bead will stay within channel 26. Then the suture ends are gripped at points intermediate the bone 10 and cup 50 so that tool 46 can be separated from the suture.

For arthroscopic procedures a length of suture is associated with a bead as described above with respect to FIGS. 5 and 6. The suture ends are passed through a conventional cannula such that the free ends are accessible to the surgeon at the proximal end of the cannula. The bead and distal end of the cannula then are inserted through an incision adjacent the site of the procedure. As fluid is circulated past the site, as conventionally occurs during arthroscopy, it passes through the cannula until the bead is forced against the cannula's distal end. After this occurs, the cannula is manipulated to cause the bead to first enter the bore 24 and then the channel 26. The cannula then is withdrawn whereby the bead remains in the channel, the suture passing through the slot and the incision.

What is claimed is:

1. A method for anchoring suture to bone, comprising:
   surgically preparing the bone by forming a slot in a cortical layer of the bone which overlays and communicates with a channel formed in a cancellous portion of the bone, the channel having a width greater than the width of the slot; and
   introducing a length of suture into the channel whereby at least one end of the suture passes through the slot, said suture including a portion within the channel which is retained against passage through the slot.

2. A method according to claim 1, wherein said suture portion is retained by a knot formed in the suture and having a width greater than the width of the slot.

3. A method according to claim 2, wherein said knot is formed at the opposite end of the suture whereby a single segment of the suture passes through the slot.

4. A method according to claim 2, wherein said knot is formed intermediate the ends of the suture whereby two segments of suture pass through the slot.

5. A method according to claim 1, further comprising:
   forming a bore in the bone which communicates with the slot and the channel.

6. A method according to claim 5, further comprising:
   introducing a bead through the bore into the channel, said bead having a width greater than the width of the slot and carrying said length of suture.

7. A method according to claim 6, wherein said suture extends through a passage formed in the bead.

8. A method according to claim 7, wherein said bead is joined to the suture intermediate the ends of the length of suture whereby two segments of the suture pass through the slot.

9. A method according to claim 6, wherein said suture is received and retained within a slot provided on the exterior of the bead.

10. A method according to claim 9, wherein said bead is joined to the suture intermediate the ends of the length of suture whereby two segments of the suture pass through the slot in the cortical layer.

11. A method according to claim 5, wherein said suture portion is retained by a knot formed in the suture and having a width greater than the width of the slot, said knot being introduced through the bore into the channel.

12. A method according to claim 11, wherein said knot is formed at the opposite end of the suture whereby a single segment of the suture passes through the slot.

13. A method according to claim 11, wherein said knot is formed intermediate the ends of the suture whereby two segments of suture pass through the slot.

* * * * *